US011253885B2

(12) United States Patent
Paunescu

(10) Patent No.: US 11,253,885 B2
(45) Date of Patent: Feb. 22, 2022

(54) ASEPTIC AEROSOL MISTING DEVICE

(71) Applicant: Johnson & Johnson Consumer Inc., Skillman, NJ (US)

(72) Inventor: Alexandru Paunescu, Skillman, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 6 days.

(21) Appl. No.: 16/506,676

(22) Filed: Jul. 9, 2019

(65) Prior Publication Data

US 2019/0329280 A1 Oct. 31, 2019

Related U.S. Application Data

(62) Division of application No. 15/337,365, filed on Oct. 28, 2016, now abandoned.

(60) Provisional application No. 62/248,699, filed on Oct. 30, 2015.

(51) Int. Cl.

| | |
|---|---|
| ***B05B 17/06*** | (2006.01) |
| ***A61M 11/00*** | (2006.01) |
| *B05B 7/24* | (2006.01) |

(52) U.S. Cl.

CPC ......... *B05B 17/063* (2013.01); *A61M 11/005* (2013.01); *B05B 17/0669* (2013.01); *B05B 7/2472* (2013.01)

(58) Field of Classification Search

CPC . B05B 17/063; B05B 17/0669; B05B 7/2472; A61M 11/005

See application file for complete search history.

(56) References Cited

U.S. PATENT DOCUMENTS

| | | | |
|---|---|---|---|
| 3,812,854 | A | 5/1974 | Michaels et al. |
| 4,004,736 | A | 1/1977 | George |
| 4,085,893 | A | 4/1978 | Durley, III |
| 4,301,968 | A | 11/1981 | Berger et al. |
| 4,696,719 | A | 9/1987 | Bischoff |
| 4,877,989 | A | 10/1989 | Drews et al. |
| 5,104,042 | A | 4/1992 | McKown |

(Continued)

FOREIGN PATENT DOCUMENTS

| | | | |
|---|---|---|---|
| BE | 1013167 | A | 10/2001 |
| CA | 2082499 | A | 11/1991 |

(Continued)

OTHER PUBLICATIONS

U.S. Appl. No. 15/337,064, filed Oct. 28, 2016, 20170128971, May 11, 2017, U.S. Pat. No. 10,239,085, Mar. 26, 2019, Grant.

(Continued)

*Primary Examiner* — Steven M Cernoch

(57) ABSTRACT

A handheld misting device includes a sonic generator, a power source coupled to the sonic generator, at least one reservoir containing a first liquid, and a conduit from the at least one reservoir. The sonic generator includes a converter and an elongate horn comprising a first horn section coupled to the converter and a second horn section physically connected to and removable from the first horn section. Sonic energy delivered to the first horn section is conducted to the second horn section. The conduit transports liquid from the at least one reservoir to the second horn section to a delivery opening distal the first horn section.

11 Claims, 2 Drawing Sheets

(56) References Cited

U.S. PATENT DOCUMENTS

| | | | |
|---|---|---|---|
| 5,166,000 A | | 11/1992 | Singh et al. |
| 5,307,640 A | | 5/1994 | Fawzy et al. |
| 5,515,842 A | | 5/1996 | Ramseyer et al. |
| 5,558,085 A | | 9/1996 | Rubsamen et al. |
| 5,632,445 A | | 5/1997 | Dubruque |
| 5,957,124 A | | 9/1999 | Lloyd et al. |
| 6,478,754 B1 | | 11/2002 | Babaev |
| 6,521,067 B1 | | 2/2003 | Clark |
| 6,601,581 B1 | | 8/2003 | Babaev |
| 6,669,103 B2 | | 12/2003 | Tsai |
| 6,748,944 B1 | | 6/2004 | DellaVecchia et al. |
| 6,837,445 B1 | | 1/2005 | Tsai |
| 6,863,224 B2 | | 3/2005 | Terada et al. |
| 6,901,926 B2 | | 6/2005 | Yamamoto et al. |
| 7,261,102 B2 | | 8/2007 | Barney et al. |
| 7,550,897 B2 | | 6/2009 | Hailes |
| 7,679,262 B2 | | 3/2010 | Meng et al. |
| 7,878,991 B2 | | 2/2011 | Babaev |
| 7,896,539 B2 | | 3/2011 | Babaev |
| 7,976,135 B2 | | 7/2011 | Brown et al. |
| 7,977,849 B2 | | 7/2011 | Hailes et al. |
| 7,992,800 B2 | | 8/2011 | Hsieh et al. |
| 8,016,209 B2 | | 9/2011 | Hess et al. |
| 8,061,629 B2 | | 11/2011 | Tranchant et al. |
| 8,123,502 B2 | | 2/2012 | Blakey et al. |
| 8,162,628 B2 | | 4/2012 | Meng et al. |
| 8,191,982 B2 | | 6/2012 | Brown et al. |
| 8,286,629 B2 | | 10/2012 | Esaki et al. |
| 8,297,947 B2 | | 10/2012 | Van Rensburg et al. |
| 8,317,299 B2 | | 11/2012 | Brown |
| 8,430,338 B2 | | 4/2013 | Duru et al. |
| 8,434,473 B2 | | 5/2013 | Tsai et al. |
| 8,720,434 B2 | | 5/2014 | Imai |
| 8,821,802 B2 | | 9/2014 | Haran |
| 8,944,344 B2 | * | 2/2015 | Donaty ................. B05B 17/063 239/102.1 |
| 8,961,496 B2 | | 2/2015 | Locke et al. |
| 9,067,427 B2 | | 6/2015 | Hayashi |
| 9,068,566 B2 | | 6/2015 | Ivri |
| 9,168,555 B2 | | 10/2015 | Tsai |
| 9,549,753 B2 | | 1/2017 | Gordon |
| 9,565,870 B2 | | 2/2017 | Deo et al. |
| 2003/0199083 A1 | | 10/2003 | Vilendrer et al. |
| 2003/0234298 A1 | | 12/2003 | Chen |
| 2004/0045547 A1 | | 3/2004 | Yamamoto |
| 2004/0123864 A1 | | 7/2004 | Hickey et al. |
| 2004/0188546 A1 | | 9/2004 | Tabata et al. |
| 2006/0243277 A1 | | 11/2006 | Denyer et al. |
| 2007/0189919 A1 | | 8/2007 | Prince et al. |
| 2007/0240706 A1 | | 10/2007 | Kobayashi et al. |
| 2008/0051693 A1 | | 2/2008 | Babaev |
| 2009/0065600 A1 | | 3/2009 | Tranchant et al. |
| 2009/0133691 A1 | | 5/2009 | Yamada et al. |
| 2009/0314853 A1 | | 12/2009 | Feriani et al. |
| 2010/0068080 A1 | | 3/2010 | Meng et al. |
| 2010/0072299 A1 | | 3/2010 | Hsieh et al. |
| 2010/0147292 A1 | | 6/2010 | Hamaguchi et al. |
| 2010/0206307 A1 | | 8/2010 | Imai |
| 2011/0268605 A1 | | 11/2011 | Haran |
| 2011/0277491 A1 | | 11/2011 | Wu et al. |
| 2011/0290241 A1 | | 12/2011 | Maeda et al. |
| 2012/0205468 A1 | | 8/2012 | Hsieh et al. |
| 2012/0279533 A1 | | 11/2012 | Kato et al. |
| 2012/0285446 A1 | | 11/2012 | Van Der Mark |
| 2012/0302979 A1 | | 11/2012 | Locke et al. |
| 2012/0304929 A1 | | 12/2012 | Ivri |
| 2012/0318260 A1 | | 12/2012 | Hsieh et al. |
| 2013/0108748 A1 | | 5/2013 | Deo et al. |
| 2013/0129392 A1 | | 5/2013 | Wakabayashi et al. |
| 2013/0307911 A1 | | 11/2013 | Hayashi |
| 2013/0319404 A1 | | 12/2013 | Feriani et al. |
| 2014/0184095 A1 | | 7/2014 | Yoshinaga et al. |
| 2014/0231538 A1 | | 8/2014 | Tabata et al. |
| 2015/0014433 A1 | | 1/2015 | Albert et al. |
| 2015/0014434 A1 | | 1/2015 | Fedorov |
| 2017/0120284 A1 | | 5/2017 | Paunescu et al. |
| 2017/0120285 A1 | | 5/2017 | Paunescu et al. |
| 2017/0128971 A1 | | 5/2017 | Paunescu et al. |
| 2017/0128972 A1 | | 5/2017 | Paunescu |

FOREIGN PATENT DOCUMENTS

| | | | | | |
|---|---|---|---|---|---|
| CN | 204951864 | U | | 1/2016 | |
| EP | 0082896 | A1 | * | 7/1983 | ......... B05B 17/0623 |
| EP | 416106 | A | | 3/1991 | |
| EP | 615470 | A | | 9/1994 | |
| EP | 2413030 | A | | 2/2012 | |
| GB | 807080 | A | | 1/1959 | |
| GB | 2099710 | A | | 12/1982 | |
| JP | S57200229 | U | | 12/1982 | |
| JP | 61057258 | A | | 2/1986 | |
| JP | 63049271 | A | | 3/1988 | |
| JP | 4267964 | A | | 9/1992 | |
| JP | 1993095673 | U | | 12/1993 | |
| JP | 8332425 | A | | 12/1996 | |
| JP | 9173925 | A | | 7/1997 | |
| JP | 10005711 | A | | 1/1998 | |
| JP | 2001149473 | A | | 6/2001 | |
| JP | 2003251239 | A | | 9/2003 | |
| JP | 2010142737 | A | | 7/2010 | |
| JP | 2012130903 | A | | 7/2012 | |
| RU | 2383358 | C | | 3/2010 | |
| WO | 1993/010910 | A | | 6/1993 | |
| WO | WO 1996/009846 | A | | 4/1996 | |
| WO | WO 2006/006963 | A | | 1/2006 | |
| WO | WO 2008/097645 | A | | 8/2008 | |
| WO | WO 2011/083380 | A | | 7/2011 | |
| WO | WO 2014/165694 | A | | 10/2014 | |
| WO | WO 2014/184095 | A | | 11/2014 | |

OTHER PUBLICATIONS

U.S. Appl. No. 15/337,325, filed Oct. 28, 2016, 20170120285, May 4, 2017, Published.
U.S. Appl. No. 62/248,682, filed Oct. 30, 2015, Expired.
U.S. Appl. No. 16/506,676, filed Jul. 9, 2019, 20190329280, Oct. 31, 2019, Published.
U.S. Appl. No. 16/506,621, filed Jul. 9, 2019, Abandoned.
U.S. Appl. No. 15/337,365, filed Oct. 28, 2016, 20170128972, May 11, 2017, Abandoned.
U.S. Appl. No. 62/248,699, filed Oct. 30, 2015, Expired.
U.S. Appl. No. 15/337,417, filed Oct. 28, 2016, 20170120284, May 4, 2017, Published.
U.S. Appl. No. 62/248,736, filed Oct. 30, 2015, Expired.
International Search Report, PCT Application No. PCT/US2016/059270, dated Jan. 12, 2017.

* cited by examiner

ASEPTIC AEROSOL MISTING DEVICE

CROSS-REFERENCE TO RELATED APPLICATION

This is a divisional of U.S. non-provisional application Ser. No. 15/337,365, filed Oct. 28, 2016, and claims the benefit of U.S. provisional application 62/248,699 filed Oct. 30, 2015. The complete disclosure of which is hereby incorporated herein by reference for all purposes.

FIELD OF THE INVENTION

The present invention relates to an aseptic misting device employing a permanent sonic generator and a replaceable liquid reservoir and nozzle.

BACKGROUND OF THE INVENTION

Spray and/or misting devices are often used to delivery cosmetic and general health care liquids. Low cost systems employ droppers and/or squeeze bottles with some form of nozzle through which the liquid is forced to provide a relatively uncontrolled dosage and droplet size.

Expensive systems may employ metering pumps and/or expensive aerosol forming components. For example, Hseih et al. U.S. Pat. No. 7,992,800 and Hseih et al. US Pub. Pat. Appn. No. 20120318260 disclose nebulizers driven by piezo-electric and/or magnetic drives to generate an aerosol mist.

Other examples include The Technology Partnership PLC, EP615470B1; Hailes et al., U.S. Pat. No. 7,550,897; and Brown et al. U.S. Pat. No. 7,976,135, which disclose liquid projection apparatus employing transducers to project liquid droplets from an outer face of a nozzle.

Finally, Terada et al. U.S. Pat. No. 6,863,224; Yamamoto et al. U.S. Pat. No. 6,901,926; and Esaki et al. U.S. Pat. No. 8,286,629 disclose ultrasonic liquid atomizing devices.

Unfortunately, these expensive components can be contaminated through repeated uses and require careful cleaning or disposal.

What is needed is a relatively low cost system for delivering controlled doses and particle/droplet size aerosol mists.

SUMMARY OF THE INVENTION

Surprisingly, we have found that ultrasonically atomizing a liquid through a sonic generator including a two-part, elongate sonic horn, wherein the distal end of the horn is disposable and has at least one submillimeter-sized nozzle disposed at the end thereof provides inexpensive aseptic atomization by separating the liquid contained in the reservoir from durable portions of the sonic generator.

In one embodiment, a handheld misting device includes a sonic generator, a power source coupled to the sonic generator, at least one reservoir containing a first liquid, and a conduit from the at least one reservoir. The sonic generator includes a converter and an elongate horn comprising a first horn section coupled to the converter and a second horn section physically connected to and removable from the first horn section. Sonic energy delivered to the first horn section is conducted to the second horn section. The conduit transports liquid from the at least one reservoir to the second horn section to a delivery opening distal the first horn section.

DETAILED DESCRIPTION OF THE PREFERRED EMBODIMENTS

The present invention relates to a handheld sonic misting device that is more economical than conventional sonic misting devices, because the relatively expensive sonic generator and horn are isolated from liquids dispensed by the misting device. In one form of these devices, the horn is formed by physically coupling two sections together—a first section is permanently coupled to the sonic generator and a second, disposable section is operatively connected to a liquid reservoir and is removably coupleable to the first section. The liquid to be dispensed is delivered from the second section at a location isolated from the first section, and the liquid dispensed from the device is directed away from the first section such that the first section is not contaminated by the liquid and subsequent liquids dispensed from the device are not contaminated by previously dispensed liquids. Examples of this system are shown below.

Figure 1:
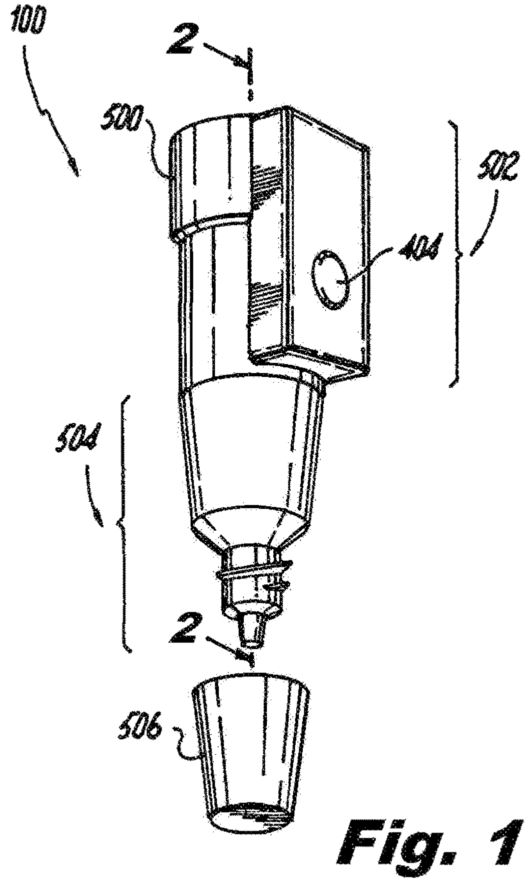
FIG. 1 is a perspective view of a handheld aseptic misting device according to one embodiment of the invention.
Figure 2:
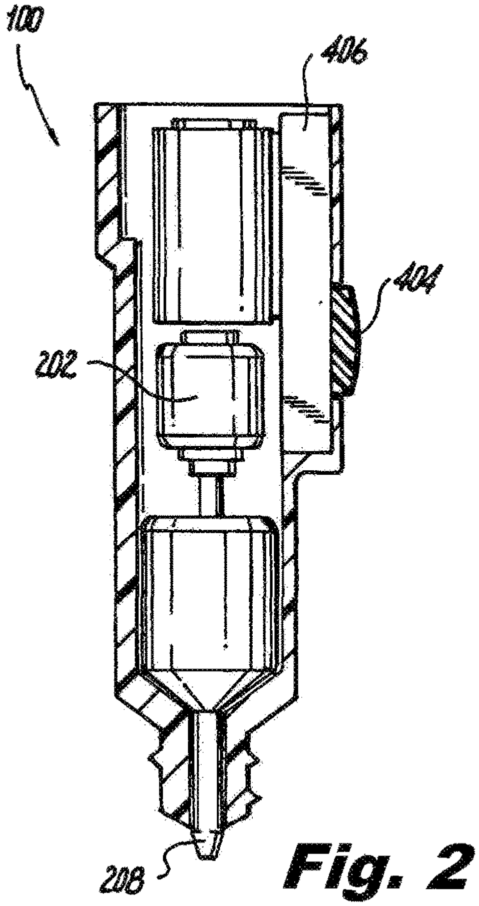
FIG. 2 is a cross-section of the handheld aseptic misting device of FIG. 1.

One embodiment of a handheld aseptic misting device is shown in FIG. 1. The handheld misting device 100 (including a sonic generator 200, a liquid delivery system 300, and an electric power and control system 400) useful to form an aerosol comprising liquid droplets (referred to herein as a “mist” or “plume”) is contained within a housing 500. The sonic generator 200 includes a converter 202 and an elongate horn 204 having a first section 206 coupled to the converter 202 and a second section 208 physically connected to and removable from the first section 206. The second section 208 has a first end 210 for connection to the first section 206 and a second, distal end 212, opposite the first end 210. The second section 208 includes a delivery opening 214 disposed at the distal end 212, an inlet port 216 disposed between the first and distal ends 210, 212 and a conduit 218 disposed within the second section 208 between the inlet port 216 and the delivery opening 214. The distal end 212 extends from the housing 500. The converter 202 is coupled to the electric power and control system 400 through electrical connections, such as wires.

The liquid delivery system 300 includes a reservoir 302 with an outlet port 304 and a conduit 306, in this embodiment, the conduit 306 is an annular space constrained by a pair of o-rings 308. The liquid is gravity fed to the outlet port 304. The conduit 306 conducts liquid from the reservoir 302 to the inlet port 216 of the second section 208 of the elongate horn 204. As indicated above, the liquid delivered to the inlet port 216 can then be dispensed to the atmosphere from the delivery opening 214.

The size, shape, and arrangement of delivery opening(s) 214 define the plume of mist generated by the misting device 100. The delivery opening(s) 214 are dimensioned to deliver an aerosol mist. Preferably, each delivery opening has a maximum dimension (across the opening) of less than about 200 microns (μm), more preferably, between about 50 and about 150 μm. Preferred delivery openings are generally circular, but one of ordinary skill in the art may modify this to achieve specifically desired aerosol properties. The number of delivery openings is selected to deliver a desired misting flow.

In order to reduce the cost of operation of the handheld misting device 100 of FIGS. 1-4, the housing 500 includes a first, electromechanical section 502 that houses components including the sonic generator 200 (including the first horn section 206) and the electric power and control system 400, and a second, liquid section 504 that houses the reservoir 302 and the second horn section 208. The liquid section 504 can be securely attached to a reusable electromechanical section 502.

The electric power and control system 400 includes a power source, such as a rechargeable battery 402, that is electrically connected to an electrical charging port (not shown) disposed in the housing 500. The electric power and control system 400 also includes an on/off switch 404, disposed on the housing 500, and one or more control boards 406. The power source is preferably replaceable and/or rechargeable and may include devices such as a capacitor or, more preferably, a battery. In a presently preferred embodiment, the power source 402 is a rechargeable battery including, without limitation, lithium-based cells, including lithium polymer batteries. One example of an internal power source is a lithium polymer cell providing a voltage of about 3.7 V that has a capacity of at least about 200 milliamp hours (mAh).

Figure 3:
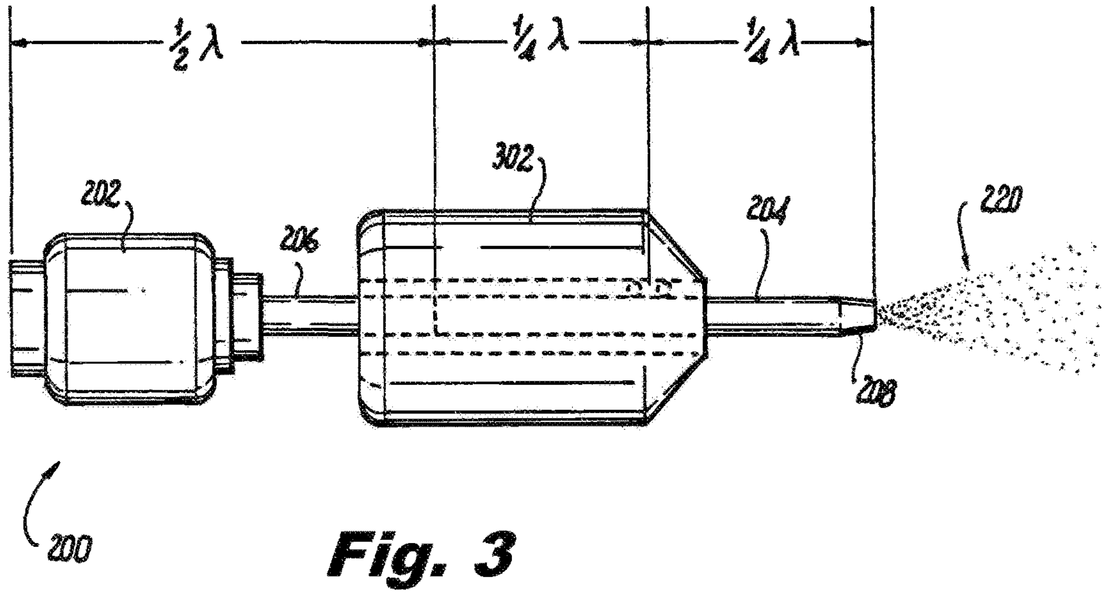
FIG. 3 is a side plan view of the sonic generator and liquid delivery system of the embodiment of FIG. 1.
Figure 4:
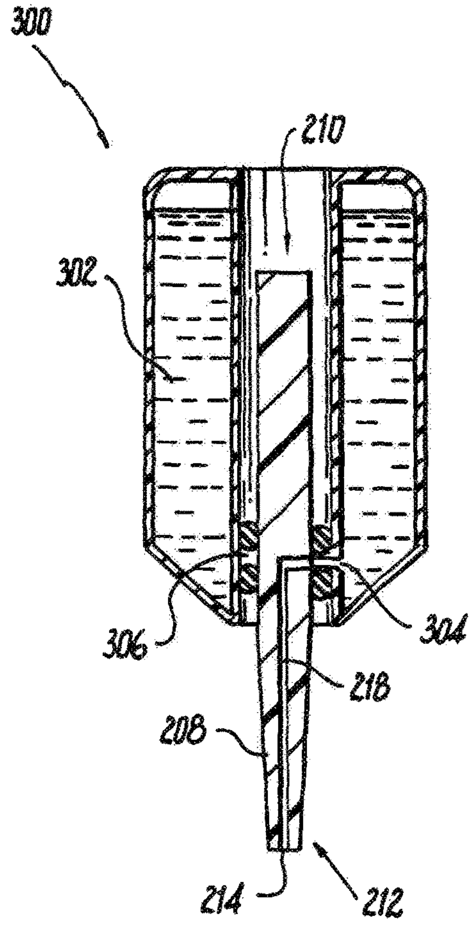
FIG. 4 is a cross section of the liquid delivery section of the embodiment of FIG. 3.

In greater detail as shown schematically in FIG. 3, the sonic generator 200 and elongate horn 204 have a length λ. The sonic generator 200 and the first section 206 of the elongate horn 204 combine to a length of approximately ½ λ, and the second section 208 also has a length of approximately ½ λ. The inlet port 216 of the second section 208 is located approximately at the midpoint of its length. Thus, the inlet port 216 of the second section 208 is approximately ¼ λ from the first end 210 that is connected to the first section 206.

Although the liquid delivery system 300 described above includes a reservoir 302 using a gravity liquid feed, one of ordinary skill in the art will recognize that other systems may be used. For example, the liquid delivery may be enhanced by including a pump or a reservoir pressurization system to force the liquid into the conduit. Alternatively, or in addition, one or more of the following may be used: pipette, syringe, collapsible reservoir, or squeezable bag.

Figure 5:
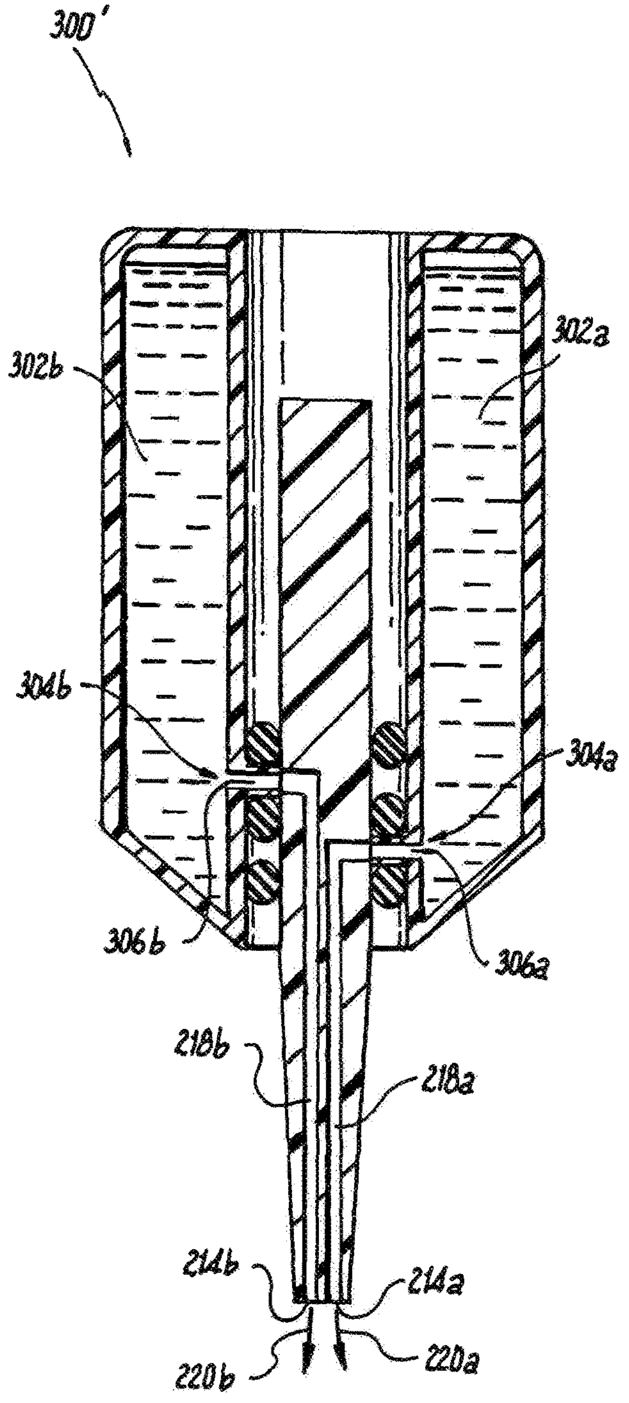
FIG. 5 is a cross section of the liquid delivery section of an alternative embodiment of the present invention.

An alternative embodiment of the liquid delivery system 300' employing an alternative second horn section 208' is shown in cross section in FIG. 5, and includes two separate reservoirs, **302*a* and 302*b*, each having an outlet port 304*a* and 304*b* in liquid communication with respective conduits 306*a* and 306*b* and second horn section conduits 218*a* and 218*b* to deliver the liquids to delivery openings 214*a* and 214*b*. Each reservoir 302*a* and 302*b* may contain a separate liquid. The system may then be used to deliver one or the other liquids, by controlling the delivery through the outlet ports 304*a* and 304*b* and ultimately the delivery openings 214*a* and 214*b*, as indicated by arrows 220*a* and 220*b*. Alternately, both liquids may be delivered simultaneously to the delivery openings 214*a* and 214*b*** to form a mixing plume formed of both liquids. In this embodiment, the system can deliver liquids that must be separated during storage.

The liquids dispensed from the device 100 may be aqueous and may include therapeutic agents, reactants, proteins, and the like.

One of ordinary skill in the art will recognize the general assembly of the handheld sonic misting device of the present invention. However, the interaction of the following elements is important to consider. First the two horn sections should interlock securely to minimize energy loss due to inefficient motion transfer therebetween to minimize heat buildup and to maximize control of the resulting aerosol plume. As the first horn section 206 is generally metallic, preferably aluminum and/or titanium, the second horn section 208 should be made of the same materials or, possibly of a compatible rigid plastic. For example in the embodiment of FIGS. 1-4, the second horn section 208 can be formed of metal or engineering plastic and machined or molded within appropriate tolerances to fit into the receptacle at the distal end of the elongate horn. A non-limiting list of useful materials include acetal resins (such as available from DuPont® Engineering Polymers under the DELRIN® brand), polyether ether ketones, amorphous thermoplastic polyetherimide (PEI) resins (such as available from SABIC under the ULTEM® brand).

The reservoir may be formed of less expensive and/or more easily handled materials, such as polyolefins, polyesters, polystyrenes, and the like.

The housing may be fabricated by plastic injection molding, or any other suitable technique, and it is preferably ergonomic and adapted to fit comfortably in a hand of a user. In a preferred embodiment, the housing has a maximum linear dimension (length) of up to about 20 cm, more preferably, up to about 15 cm, and most preferably up to about 10 cm. Preferably, the maximum dimension perpendicular to the length is 8 cm, more preferably, 5 cm.

In a preferred embodiment, the liquid section 504 is removable from the electromechanical section 502 in a manner in which the two horn sections interlock securely.

The present invention is useful in the delivery of aerosol plumes of medication and/or moisturizing solutions in a more sanitary manner than currently provided. Sonic generation of aerosol plumes can provide very fine mists, having a droplet size between about 20 and about 60 μm, given by the practical range of frequencies for the ultrasonic horn between 20 kHz and 200 kHz. As indicated above, as sonic generators are more expensive than traditional squeeze and spray bottles, it is important to separate the expensive and reusable sonic generator and horns from the relatively inexpensive and potentially disposable liquid reservoirs. Therefore, in use, a replaceable liquid section 502, can be slidably inserted into or threaded onto the electromechanical section 504. Any protective covering (e.g., cap 506) can be removed from the delivery opening(s) 214, and the misting device 100 can be energized.

To create an aerosol plume, the switch 404 is depressed, and the sonic generator 200 provides energy to the elongate horn 204. The liquid from the reservoir 302 is drawn into the conduit 306 and horn conduit 218 to deliver liquid to the delivery opening(s) 214. This sequence may be repeated until the reservoir is emptied. The now-empty liquid section 504 can be removed and a new liquid section 504, including a new second horn section 208 and delivery opening(s) 214, is attached. The new second horn section 208 and delivery opening(s) 214 are not contaminated as a result of the previous use of the misting device.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. A handheld misting device comprising:

a) a sonic generator comprising a converter and an elongate horn comprising a first horn section coupled to the converter and a second horn section physically connected to and removable from the first horn section arranged and configured to form a single, linear elongate horn, whereby sonic energy delivered to the first horn section is conducted to the second horn section;

b) a power source coupled to the sonic generator;

c) a first reservoir containing a first liquid;

d) a first conduit having an inlet from the first reservoir to deliver the first liquid through the second horn section to a first delivery opening dimensioned to deliver an aerosol mist distal the first horn sections;

e) a second reservoir containing a second liquid, different than the first liquid;

f) a second conduit having an inlet from the second reservoir to deliver the second liquid through the second horn section to a second delivery opening dimensioned to deliver an aerosol mist, proximate the first delivery opening;

wherein each of the first and second conduit inlets has a central axis, each of the first and second delivery openings has a central axis and the central axes of the inlets and delivery openings of the respective conduits are offset by an angle greater than zero degrees and wherein the second horn section has a length and the first and second conduit inlets are displaced along the length of the second horn section and are separated by at least one seal.

2. The handheld misting device of claim 1 wherein the first and second reservoirs and second horn section are disposable.

3. The handheld misting device of claim 1 wherein at least one of the first and second liquids is aqueous.

4. The handheld misting device of claim 1 wherein the first and second liquids comprise reactants.

5. The handheld misting device of claim 1 wherein the first and second liquids comprise proteins.

6. A handheld misting device comprising:

a) a sonic generator comprising a converter and an elongate horn consisting essentially of a single first horn section coupled to the converter and a second horn section physically connected to and removable from the first horn section arranged and configured to form a single, linear elongate horn, the second horn section comprising at least a first and a second conduit, whereby sonic energy delivered to the first horn section is conducted to the second horn section;

b) a power source coupled to the sonic generator;

c) a first reservoir containing a first liquid operatively connected to an inlet of the first conduit to deliver the first liquid through the second horn section to a first delivery opening dimensioned to deliver an aerosol mist distal the first horn section;

d) a second reservoir containing a second liquid operatively connected to an inlet of the second conduit to deliver the second liquid through the second horn section to a second delivery opening dimensioned to deliver an aerosol mist, proximate the first delivery opening;

wherein each of the first and second conduit inlets has a central axis, each of the first and second delivery openings has a central axis and the central axes of the inlets and delivery openings of the respective conduits are offset by an angle greater than zero degrees and wherein the second horn section has a length and the first and second conduit inlets are displaced along the length of the second horn section and are separated by at least one seal.

7. The handheld misting device of claim 6 wherein the first and second reservoirs and second horn section are disposable.

8. The handheld misting device of claim 6 wherein at least one of the first and second liquids is aqueous.

9. The handheld misting device of claim 6 wherein the first and second liquids comprise reactants.

10. The handheld misting device of claim 6 wherein the first and second liquids comprise proteins.

11. The handheld misting device of claim 6 wherein the second liquid is different than the first liquid.

* * * * *